United States Patent
Kim et al.

(10) Patent No.: US 9,431,617 B2
(45) Date of Patent: Aug. 30, 2016

(54) PHOSPHORESCENT COMPOUND AND ORGANIC LIGHT EMITTING DIODE DEVICE USING THE SAME

(71) Applicant: LG DISPLAY CO., LTD., Seoul (KR)

(72) Inventors: Jung-Keun Kim, Seoul (KR); In-Bum Song, Seoul (KR); Bo-Min Seo, Seoul (KR); Jae-Hyung Yu, Hanam-si (KR)

(73) Assignee: LG DISPLAY CO., LTD., Seoul (KR)

( * ) Notice: Subject to any disclaimer, the term of this patent is extended or adjusted under 35 U.S.C. 154(b) by 311 days.

(21) Appl. No.: 13/973,779

(22) Filed: Aug. 22, 2013

(65) Prior Publication Data

US 2014/0151649 A1  Jun. 5, 2014

(30) Foreign Application Priority Data

Dec. 3, 2012  (KR) .......... 10-2012-0138993

(51) Int. Cl.
| | |
|---|---|
| *H01L 51/00* | (2006.01) |
| *C07F 7/08* | (2006.01) |
| *C07F 7/10* | (2006.01) |
| *C09K 11/06* | (2006.01) |

(52) U.S. Cl.
CPC ......... *H01L 51/0094* (2013.01); *C07F 7/0814* (2013.01); *C07F 7/10* (2013.01); *C09K 11/06* (2013.01); *C09K 2211/1022* (2013.01); *C09K 2211/1029* (2013.01); *H01L 51/0085* (2013.01); *H01L 2251/308* (2013.01)

(58) Field of Classification Search
None
See application file for complete search history.

(56) References Cited

U.S. PATENT DOCUMENTS

| | | | |
|---|---|---|---|
| 8,373,159 B2 | 2/2013 | Langer et al. | |
| 8,697,255 B2 | 4/2014 | Langer et al. | |
| 2002/0055013 A1 | 5/2002 | Kim et al. | |
| 2005/0238919 A1* | 10/2005 | Ogasawara | C09K 11/06 428/690 |
| 2009/0123173 A1 | 5/2009 | Kadowaki | |
| 2011/0031477 A1* | 2/2011 | Langer | C09K 11/06 257/40 |

FOREIGN PATENT DOCUMENTS

| | | |
|---|---|---|
| CN | 101688114 A | 3/2010 |
| CN | 101878552 A | 11/2010 |
| CN | 102341403 A | 2/2012 |
| JP | 2003226871 A | 8/2003 |

\* cited by examiner

*Primary Examiner* — J. L. Yang
(74) *Attorney, Agent, or Firm* — Birch, Stewart, Kolasch & Birch, LLP

(57) ABSTRACT

The present invention provides a phosphorescent compound of following formula:

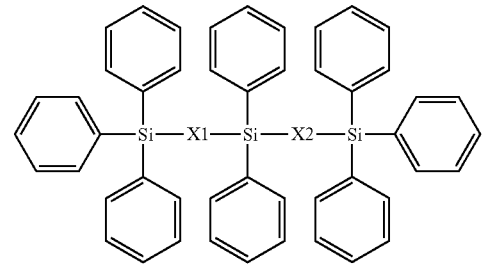

wherein each of X1 and X2 is independently selected from substituted or non-substituted carboline, dibenzofuran, dibenzothiophene and fluorene.

11 Claims, 2 Drawing Sheets

PHOSPHORESCENT COMPOUND AND ORGANIC LIGHT EMITTING DIODE DEVICE USING THE SAME

The present application claims the benefit of Korean Patent Application No. 10-2012-0138993 filed in Korea on Dec. 3, 2012, which is herein incorporated by reference.

BACKGROUND OF THE INVENTION

1. Field of the Invention

The present invention relates to a phosphorescent compound and an organic light emitting diode (OLED) device and more particularly to a phosphorescent compound having improved emitting efficiency due to high triplet energy and an OLED device using the same.

2. Discussion of the Related Art

Recently, requirement for flat panel display devices having small occupied area is increased. Among the flat panel display devices, an OLED device, which may be called to as an organic electroluminescent device, is widely introduced.

The OLED device emits light by injecting electrons from a cathode as an electron injection electrode and holes from an anode as a hole injection electrode into an emission compound layer, combining the electrons with the holes, generating an exciton, and transforming the exciton from an excited state to a ground state. A flexible substrate, for example, a plastic substrate, can be used as a base substrate where elements are formed. Since the OLED device does not require a backlight assembly, the OLED device has low weight and low power consumption. Moreover, the OLED device can be operated at a voltage (e.g., 10V or below) lower than a voltage required to operate other display devices. In addition, the OLED device is adequate to produce full-color images.

A general method for fabricating OLED device will be briefly explained below.

(1) First, an anode is formed on a substrate by depositing a transparent conductive compound, for example, indium-tin-oxide (ITO).

(2) Next, a hole injecting layer (HIL) is formed on the anode. For example, the HIL may be formed of 4,4'-bis[N-[4-{N,N-bis(3-methylphenyl)amino}phenyl]-N-phenylamino]biphenyl (DNTPD), which is represented in following Formula 1-1, and have a thickness of about 10 nm to about 60 nm.

(3) Next, a hole transporting layer (HTL) is formed on the HIL. For example, the HTL may be formed of 4,4'-bis[N-(1-naphtyl)-N-phenylamino]-biphenyl (NPB), which is represented in following Formula 1-2, and have a thickness of about 30 nm to about 60 nm. In the OLED device using the phosphorescent compound, an electron blocking layer may be formed on the HTL by a thickness of about 5 nm to 10 nm to increase emission efficiency and lifetime.

(4) Next, an emitting compound layer (EML) is formed on the HTL. A dopant may be doped onto the EML. In a phosphorescent type, the EML may be formed of 4,4'-N,N'-dicarbaxole-biphenyl (CBP), which is represented in following Formula 1-3, and have a thickness of about 30 nm to about 60 nm, and tris((3,5-difluoro-4-cyanophenyl)pyridine)irdium(III) (FCNIr), which is represented in following Formula 1-4, as the dopant may be doped to form a blue emitting material pattern. In addition, for displaying full color image, red and green emitting material patterns are formed.

(5) Next, an electron transporting layer (ETL) and an electron injecting layer (EIL) are stacked on the EML. In the OLED device using the phosphorescent compound, a hole blocking layer may be formed before forming the ETL by a thickness of about 5 nm to 10 nm to keep the triplet exciton in the EML.

(6) A cathode is formed on the EIL, and a passivation layer is formed on the cathode.

[Formula 1-1]

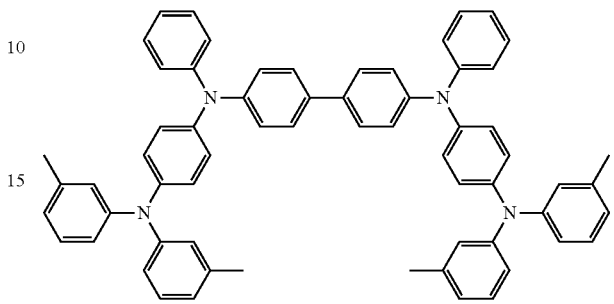

[Formula 1-2]

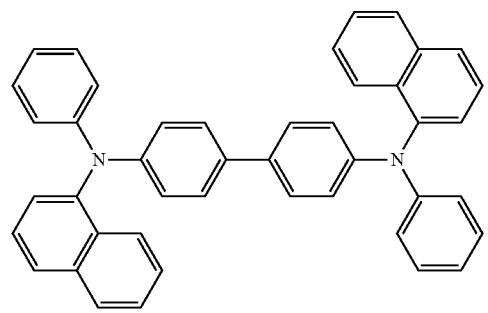

[Formula 1-3]

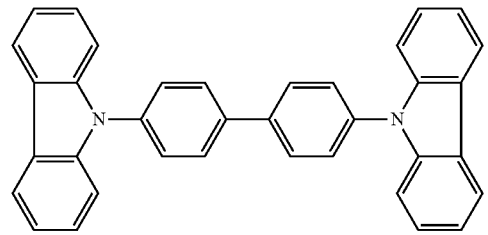

[Formula 1-4]

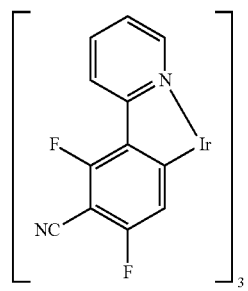

Recently, a phosphorescent compound is more widely used for the emission layer than a fluorescent compound. The fluorescent compound only uses singlet energy corresponding to about 25% of excitons for emitting light, and triplet energy corresponding to about 75% of excitons is lost as a heat. However, the phosphorescent compound uses not only the singlet energy but also the triplet energy for emitting light. The phosphorescent dopant includes a heavy atom, such as iridium (Ir), at a center of an organic compound and has a high electron transition probability from the triplet state to the single state.

However, the efficiency of the dopant is rapidly decreased because of a quenching phenomenon such that there is a limitation in the emitting material layer of the dopant without a host. Accordingly, it is desired to form the emitting material layer by the dopant with the host having higher thermal stability and triplet energy.

In the OLED device including the phosphorescent compound, a hole from anode and an electron from the cathode combine at the host of the emitting material layer. Energy transition of a singlet exciton from the host into a singlet or triplet energy level of the dopant is generated, and energy transition of a triplet exciton from the host into the triplet energy level of the dopant is generated. The exciton into the singlet energy level of the dopant is transited again into the triplet energy level of the dopant. Namely, all excitons are transited into the triplet energy level of the dopant. The excitons in the triplet energy level of the dopant are transited into a ground state such that the emitting material layer emits light.

For an efficient energy transition into the dopant, a triplet energy of the host should be larger than that of the dopant. When the triplet energy of the host is smaller than that of the dopant, an energy counter-transition from the dopant to the host is generated such that an emission efficiency is reduced. The triplet energy is an important fact in the HTL and the ETL as well as the host and the dopant.

Referring to FIG. 1, CBP, which is widely used for the host, has a triplet energy level of about 2.6 eV, which is larger than that of Firpic or FCNIr, which are used as a blue dopant, such that emission efficiency is reduced.

Accordingly, new blue phosphorescent compound having the triplet energy larger than that of the phosphorescent dopant is required.

SUMMARY OF THE INVENTION

Accordingly, the present invention is directed to a phosphorescent compound and an OLED device using the same that substantially obviate one or more of the problems due to limitations and disadvantages of the related art.

An object of the present invention is to provide a phosphorescent compound having high triplet energy.

Another object of the present invention is to provide an OLED having improved emission efficiency.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described herein, the present invention provides a phosphorescent compound of following formula:

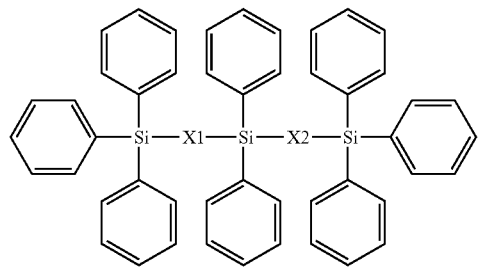

wherein each of X1 and X2 is independently selected from substituted or non-substituted carboline, dibenzofuran, dibenzothiophene and fluorene.

In another aspect of the present invention, the present invention provides an organic light emitting diode device including a first electrode; a second electrode facing the first electrode; an emitting material layer between the first and second electrodes; a hole transporting layer between the first electrode and the emitting material layer; and an electron transporting layer between the second electrode and the emitting material layer, wherein at least one of the emitting material layer and the electron transporting layer includes a phosphorescent compound of following formula, and each of X1 and X2 is independently selected from substituted or non-substituted carboline, dibenzofuran, dibenzothiophene and fluorene.

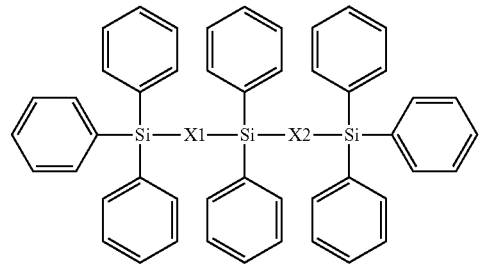

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE PREFERRED EMBODIMENTS

Figure 1:
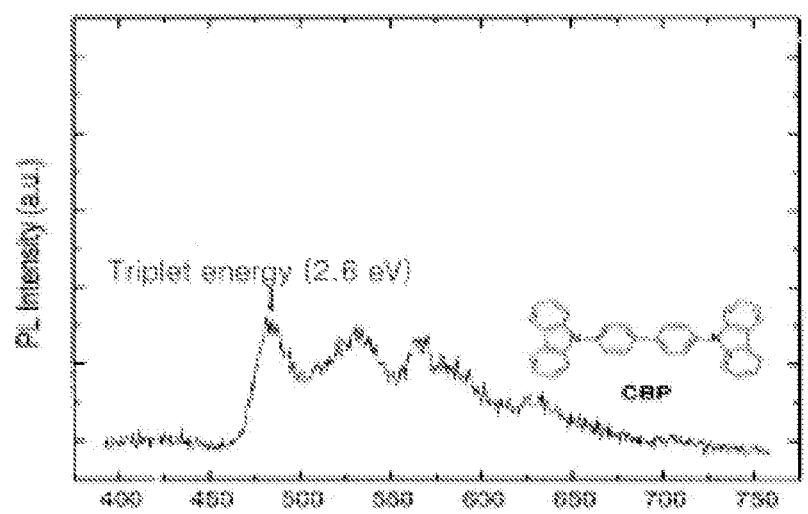
FIG. 1 is a graph showing a photoluminescence (PL) spectrum of CBP as a host for the related art OLED device.

Reference will now be made in detail to the preferred embodiments, examples of which are illustrated in the accompanying drawings.

A phosphorescent compound according to the present invention is represented by following Formula 2. The phosphorescent compound includes carboline, dibenzofuran, dibenzothiophene and fluorene, which have a high electron-transporting property, and a silane core, which is capable of separating π-conjugation. As a result, the phosphorescent compound in the present invention has high triplet energy and electron-transporting property.

[Formula 2]

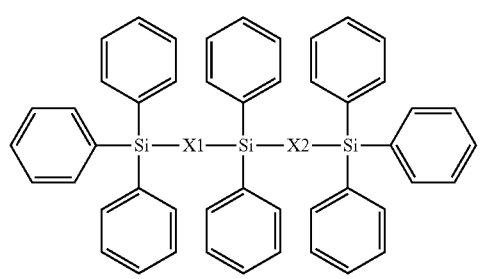

In the above Formula 2, each of X1 and X2 is independently selected from substituted or non-substituted carboline, dibenzofuran, dibenzothiophene and fluorene. X1 and X2 are same or different. For example, the substituent of each of carboline, dibenzofuran, dibenzothiophene and fluorene may be one of C6~C12 alkyl, C6~C12 aryl and pyridine.

For example, each of X1 and X2 may be selected from materials in following Formula 3.

[Formula 3]

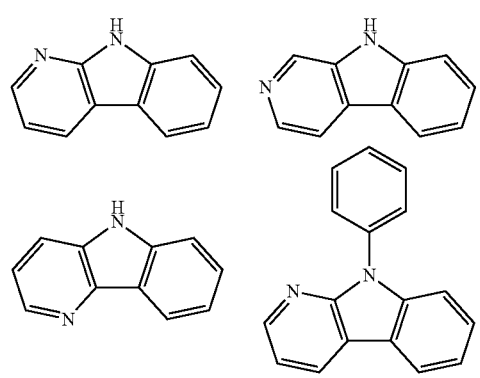

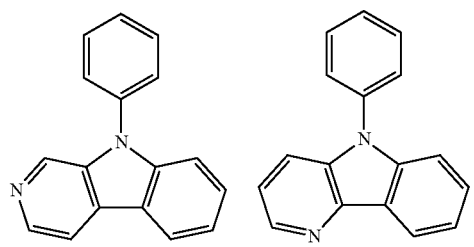

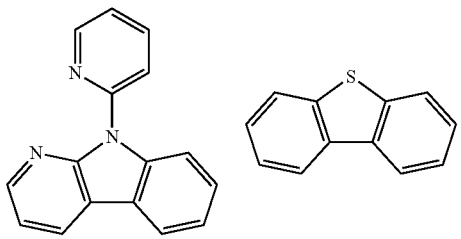

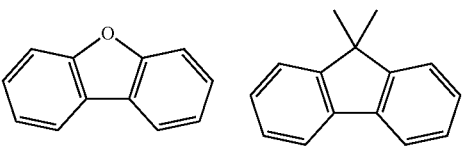

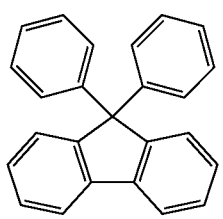

For example, the phosphorescent compound of the above Formula 2 may be one of materials in following Formula 4.

[Formula 4]

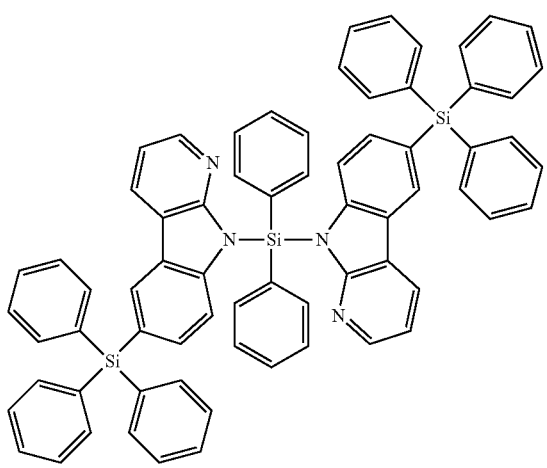

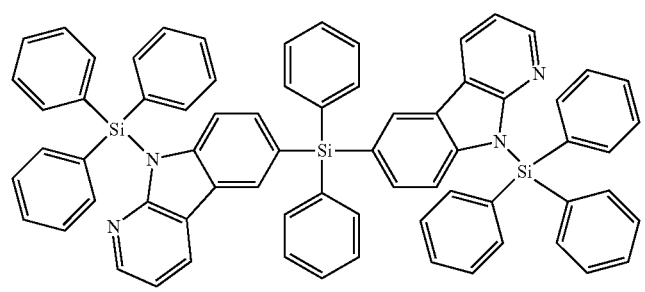

-continued
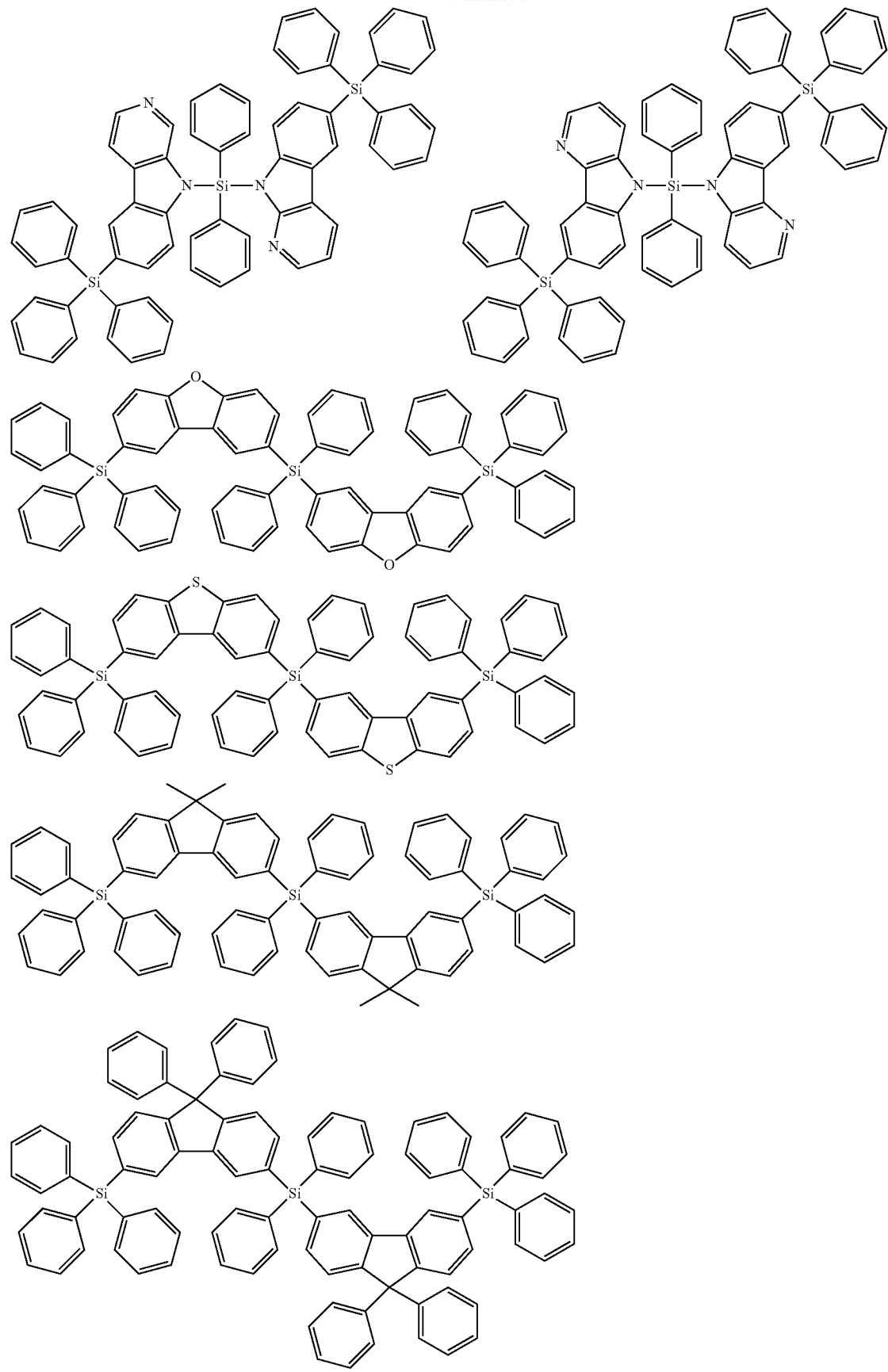

-continued
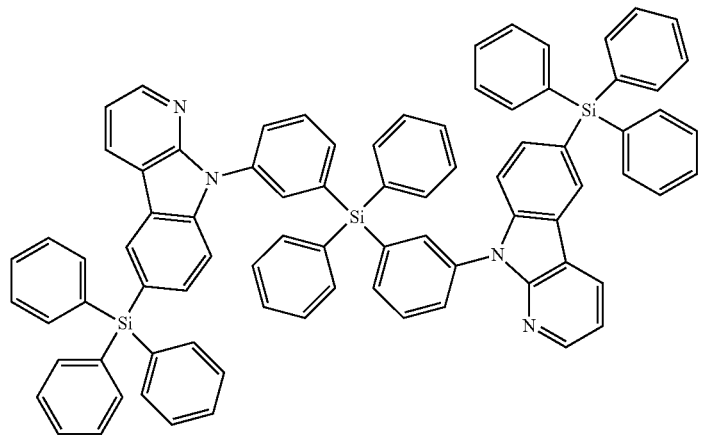
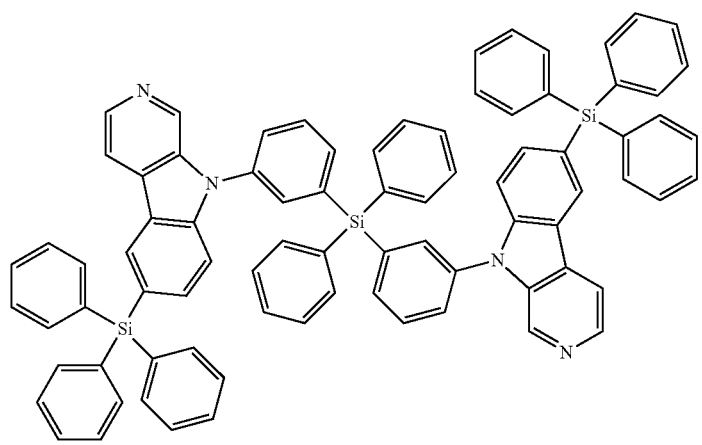
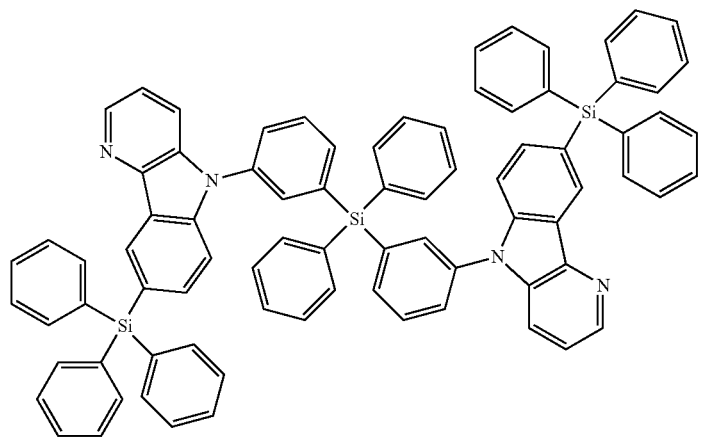 [SMILES: c1ccc([Si](c2ccccc2)(c2ccccc2)c2ccc3c(c2)c2ccncc2n3-c2cccc([Si](c3ccccc3)(c3ccccc3)c3cccc(-n4c5ccc([Si](c6ccccc6)(c6ccccc6)c6ccccc6)cc5c5ccncc54)n3)n2)cc1]

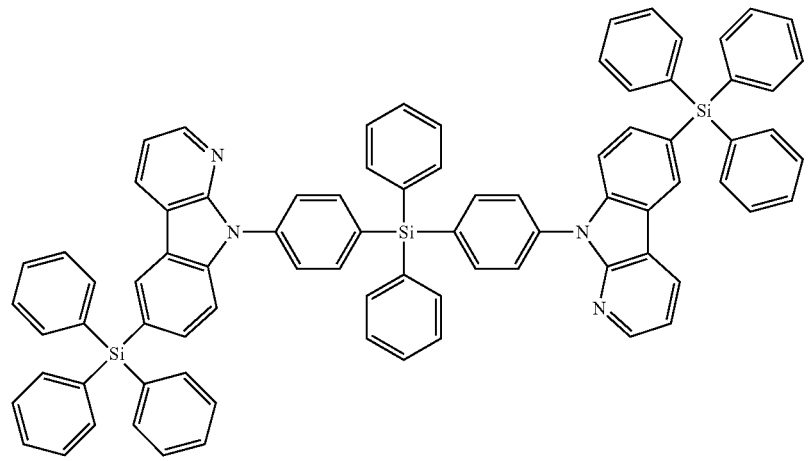
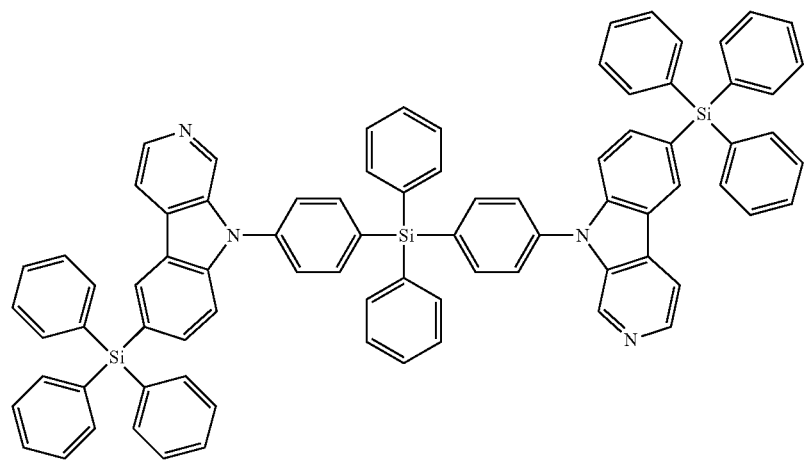
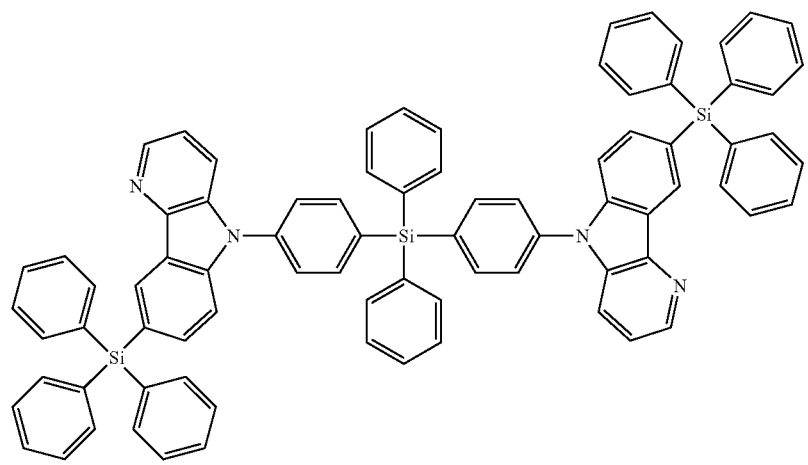

-continued

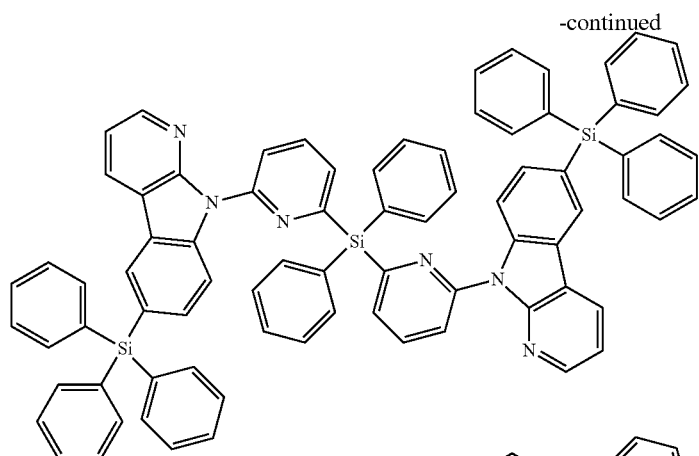

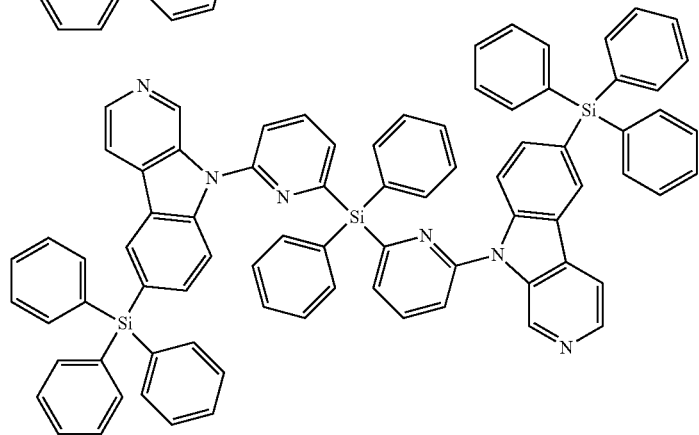

The phosphorescent compound of the present invention has high triplet energy due to silane core being capable of separating π-conjugation. Accordingly, emission efficiency decrease resulting from an energy counter-transition problem from the dopant to the host is prevented.

In addition, since the phosphorescent compound includes the material group having a high electron-transporting property, e.g., carboline, dibenzofuran, dibenzothiophene and fluorene, the phosphorescent compound is adequate to the hole blocking layer or the electron transporting layer.

Hereinafter, synthesis and properties of the "A-1", "A-2" and "A-3" compounds in following Formula 5 are explained.

A-1

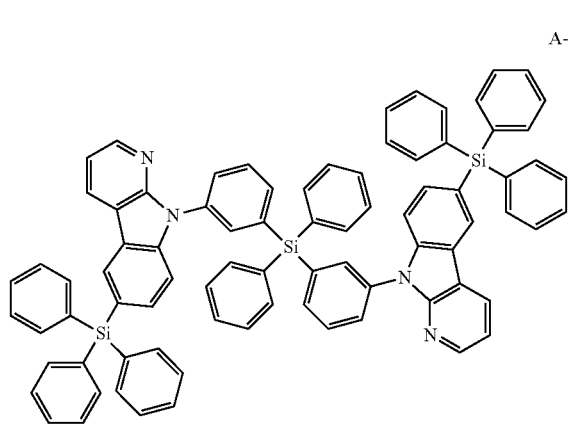

-continued

A-2

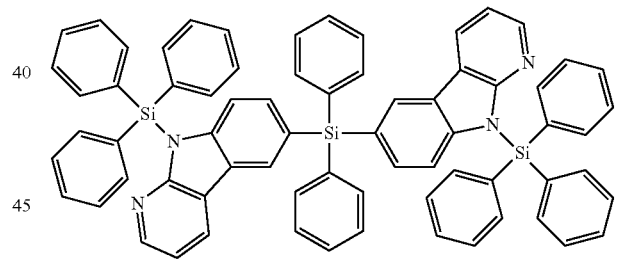

A-3

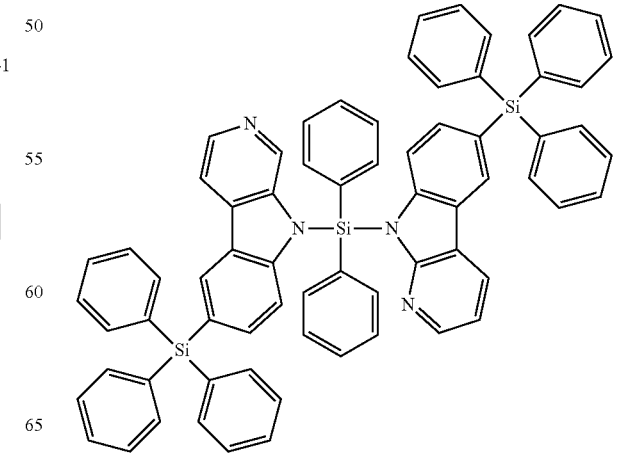

The "A-1" compound (9-(3-(diphenyl(3-(6-(triphenylsilyl)-9H-pyrido[2,3-b]indol-9-yl)phenyl)silyl)phenyl)-6-(triphenylsilyl)-9H-pyrido[2,3-b]indole) is synthesized by following synthesis.

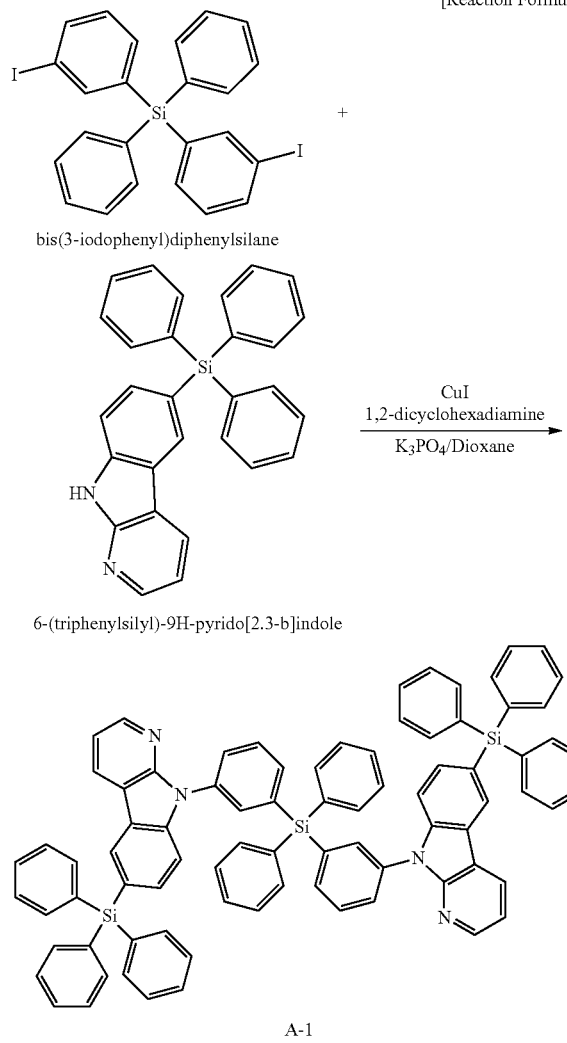

A-1

Bis(3-iodophenyl)diphenylsilane 1.2 g (2.04 mmol), 6-(triphenylsilyl)-9H-pyrido[2,3-b]indole (4.5 mmol), K$_3$PO$_4$ (7 mmol), CuI (1 mmol), trans-1,2-cyclohexanediamine (1 mmol) and 1,4-dioxane (50 ml) were put in a 100 ml two-neck flask and refluxed for about 24 hours. After completion of the reaction, the reaction mixture was distilled under a reduced pressure to remove 1,4-dioxane. After the resultant was extracted using dichloromethane and water and distilled under a reduced pressure, silica-gel column was performed and distillation under a reduced pressure was performed. The resultant was re-crystallized using dichloromethane and petroleum ether and filtered to obtain white powders ("A-1" compound, 0.8 g).

Figure 2:
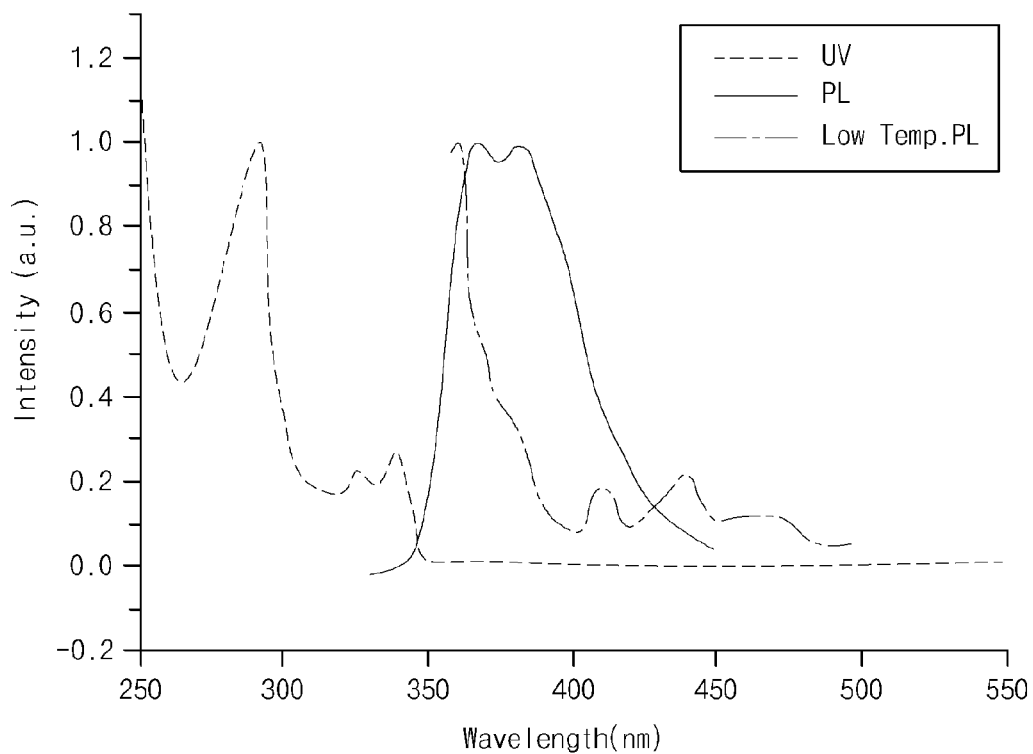
FIG. 2 is a graph showing a UV spectrum and low and room temperature PL spectrums of a phosphorescent compound according to the present invention.

A UV spectrum and low and room temperature PL spectrums of the "A-1" compound are shown in FIG. 2. Properties of the related art phosphorescent compound "CBP" and the phosphorescent compounds "A-1", "A-2" and "A-3" in Formula 5 are listed in Table 1.

TABLE 1

| | HOMO (eV) | LUMO (eV) | Band gap energy (eV) | E$_T$(eV) |
|---|---|---|---|---|
| CBP | −6.0 | −2.5 | 3.5 | 2.6 |
| A-1 | −5.98 | −2.52 | 3.53 | 3.02 |
| A-2 | −6.1 | −2.43 | 3.57 | 3.04 |
| A-3 | −6.0 | −2.48 | 3.52 | 3.03 |

As shown in FIG. 2 and Table 1, the phosphorescent compounds "A-1", "A-2" and "A-3" of the present invention has the triplet energy (E$_T$), above 3.0 eV, higher than that of the related art phosphorescent compound "CBP".

Hereinafter, a detailed description will be made of preferred examples associated with the OLED device according to the present invention. More specifically, the examples relate to an OLED device including an emission material layer which uses the phosphorescent compound of Formula 2 as a host.

EXAMPLES

Example

An ITO layer is deposited and patterned to have an area of 3 mm*3 mm on a substrate and washed to form an anode. The substrate is loaded in a vacuum chamber, and a hole injecting layer (50 Å) of hexaazatriphenylene-hexacarbonitrile (HAT-CN), a hole transporting layer (550 Å) of 4-4'-bis[N-(1-naphtyl)-N-phenylamino]-biphenyl (NPB), an electron blocking layer (100 Å) of di-(4-(N,N'-ditolylamino)-phenyl)cyclohexane (TAPC), an emitting material layer (300 Å) of the "A-1" phosphorescent compound in the above Formula 5 and a blue dopant (15%) of FCNIr, an electron transporting layer (400 Å) of TmPyPB, an electron injecting layer (5 Å) of LiF, and a cathode (1100 Å) of aluminum are sequentially formed on the anode.

Comparative Example

An ITO layer is deposited on a substrate and washed to form an anode. The substrate is loaded in a vacuum chamber, and a hole injecting layer (50 Å) of HAT-CN, a hole transporting layer (550 Å) of NPB, an electron blocking layer (100 Å) of TAPC, an emitting material layer (300 Å) of the reference host in following Formula 6 and a blue dopant (15%) of FCNIr, an electron transporting layer (400 Å) of TmPyPB, an electron injecting layer (5 Å) of LiF, and a cathode (1100 Å) of aluminum are sequentially formed on the anode.

[Formula 6]

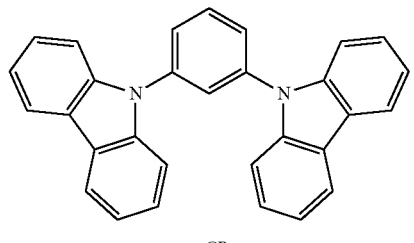

mCP

Properties of the OLED device of the comparative example and the example are listed in Table 2.

TABLE 2

| | V | J (mA/cm2) | Quantum efficiency (%) | Cd/A | Lm/W | CIE (x) | CIE (y) |
|---|---|---|---|---|---|---|---|
| Comparative example | 6.05 | 10 | 7.7 | 13.5 | 7.13 | 0.156 | 0.285 |
| example | 5.8 | 10 | 10.8 | 16.8 | 9.1 | 0.156 | 0.252 |

Referring to Table 2, the OLED device using the phosphorescent compound of the present invention has advantages in emitting efficiency, driving voltage and so on. In addition, the OLED device using the phosphorescent compound of the present invention has excellent color sensitivity due to lower CIE(y) value. Namely, in comparison to the mCP host material, which has a relatively high triplet energy in the related art host material, the phosphorescent compound in the present invention has advantages in emitting efficiency, driving voltage and color sensitivity such that the OLED device can be operated in lower driving voltage and display high quality images.

Figure 3:
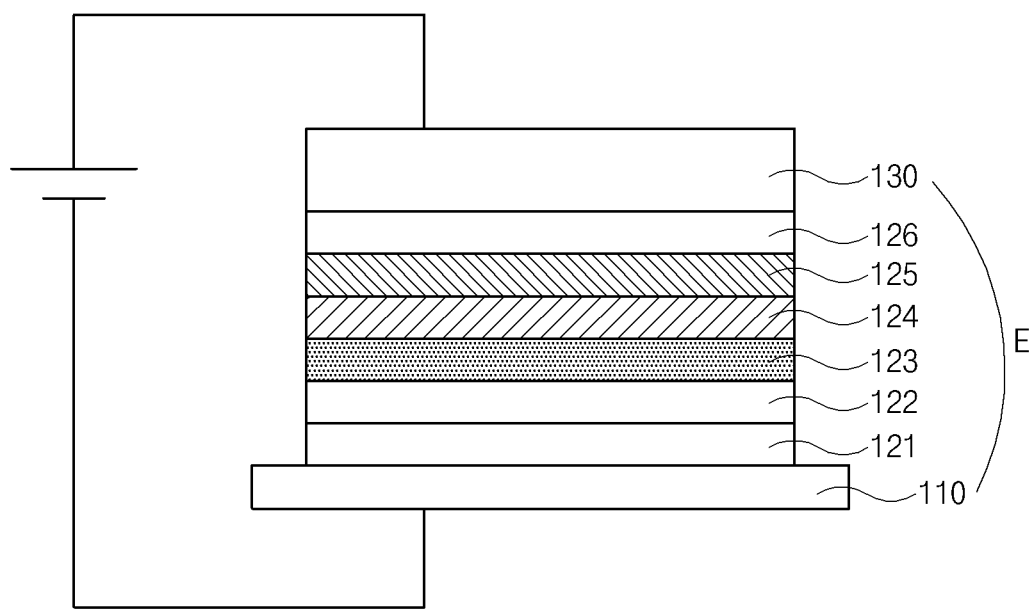
FIG. 3 is a schematic cross-sectional view of an OLED device according to the present invention.

Referring to FIG. 3, which is a schematic cross-sectional view of an OLED device according to the present invention, the OLED device includes a first substrate (not shown), a second substrate (not shown) and an organic emitting diode E between the first and second substrates.

The organic emitting diode E includes a first electrode 110, a second electrode 130 and an organic emitting layer 120. The first electrode 110 is formed of a material having a relatively high work function to serve as an anode. For example, the first electrode 110 may be formed of indium-tin-oxide (ITO). The second electrode 130 is formed of a material having a relatively low work function to serve as a cathode. For example, the second electrode 130 may be formed of aluminum (Al) or Al alloy.

The organic emitting layer 120 includes red, green and blue organic emitting pattern. To increase emission efficiency, the organic emitting layer 120 includes a hole injecting layer (HIL) 121, a hole transporting layer (HTL) 122, an emitting material layer (EML) 123, an electron transporting layer (ETL) 125 and an electron injecting layer (EIL) 126. In addition, to keep the triplet exciton in the emitting material layer 123, the organic emitting layer 120 may further include a hole blocking layer 124 between the electron transporting layer 125 and the emitting material layer 123.

At least one of the emitting material layer 123, the hole blocking layer 124 and the electron transporting layer 125 includes the phosphorescent compound in the above Formula 2.

For example, when the emitting material layer 123 includes the phosphorescent compound in the above Formula 2 as a host, a dopant is doped by about 1 to 30 wt % such that the emitting material layer 123 emits blue light. Since the phosphorescent compound as the host has the triple energy, i.e. above 3.0 eV, larger than the dopant, an energy counter-transition from the dopant to the host is prevented. As a result, emission efficiency is improved.

On the other hand, when the hole blocking layer 124 and the electron transporting layer 125 includes the phosphorescent compound in the above Formula 2, an energy counter-transition from the dopant to the blocking layer 124 and the electron transporting layer 125 is prevented because the phosphorescent compound in the above Formula 2 has the triple energy larger than the dopant. In addition, since the phosphorescent compound has the high electron-transporting property, the triplet exciton is kept in the emitting material layer 123 by the hole blocking layer 124 and the electron is efficiently transported by the electron transporting layer 125. As a result, emission efficiency is further improved.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A phosphorescent compound of formula 1:

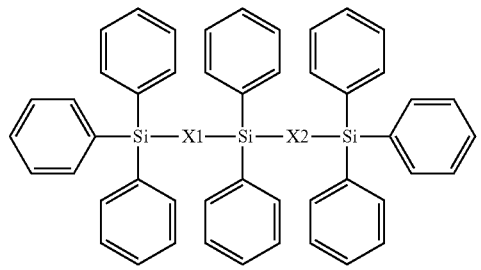

wherein each of X1 and X2 is independently selected from substituted or non-substituted carboline, dibenzothiophene, fluorene and dibenzofuran, and at least one of X1 and X2 is selected from substituted or non-substituted carboline.

2. The compound according to claim 1, wherein the substituent of carboline, dibenzothiophene, fluorene and dibenzofuran is one of C6~C12 alkyl, C6~C12 aryl and pyridine.

3. An organic light emitting diode device, comprising:
a first electrode;
a second electrode facing the first electrode;
an emitting material layer between the first and second electrodes;
a hole transporting layer between the first electrode and the emitting material layer; and
an electron transporting layer between the second electrode and the emitting material layer,
wherein at least one of the emitting material layer and the electron transporting layer includes a phosphorescent compound of formula 1, and each of X1 and X2 is independently selected from substituted or non-substituted carboline, dibenzothiophene, fluorine and dibenzofuran:

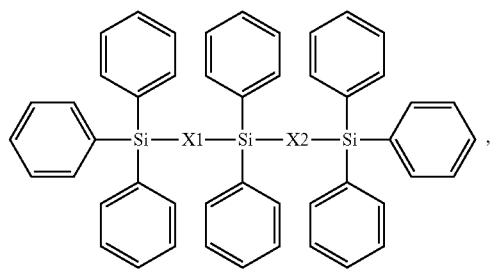

and at least one of X1 and X2 is selected from substituted or non-substituted carboline.

4. The device according to claim 3, wherein the substituent of carboline, dibenzothiophene, fluorene and dibenzofuran is one of C6~C12 alkyl, C6~C12 aryl and pyridine.

5. The device according to claim 3, further comprising a hole blocking layer between the emitting material layer and the electron transporting layer, wherein hole blocking layer includes the phosphorescent compound.

6. The compound according to claim 1, wherein each of X1 and X2 is independently selected from the group consisting of:

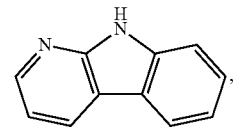, 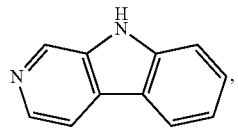,

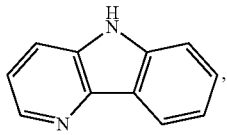, 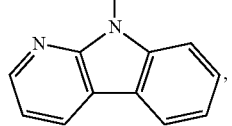,

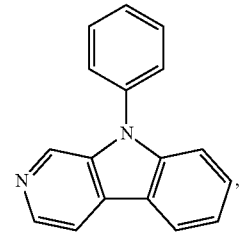, 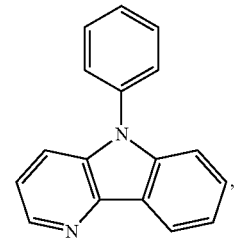,

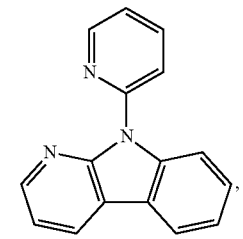, 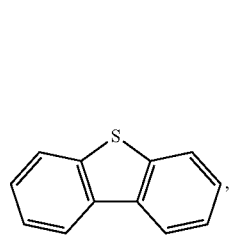,

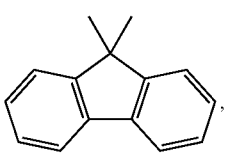, , and

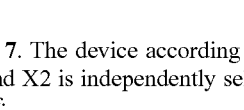, 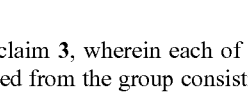.

7. The device according to claim 3, wherein each of X1 and X2 is independently selected from the group consisting of:

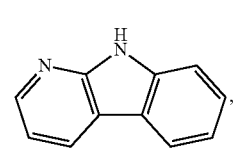, 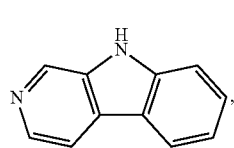,

-continued

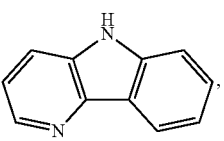, 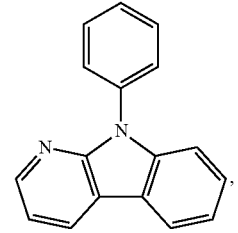,

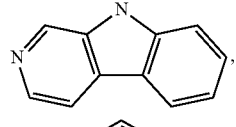, 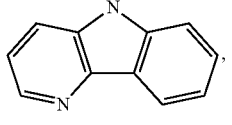,

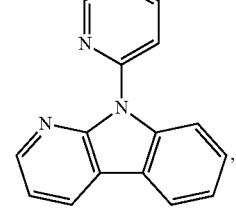, 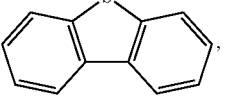,

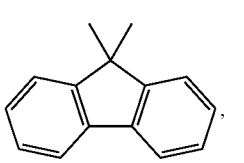, 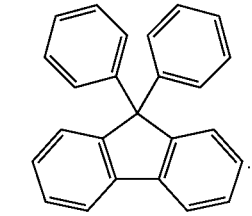,

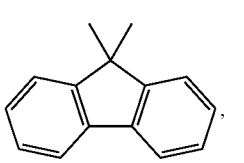, and 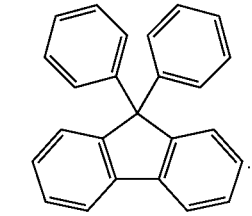.

8. The compound according to claim 1, wherein the phosphorescent compound is selected from the group consisting of:

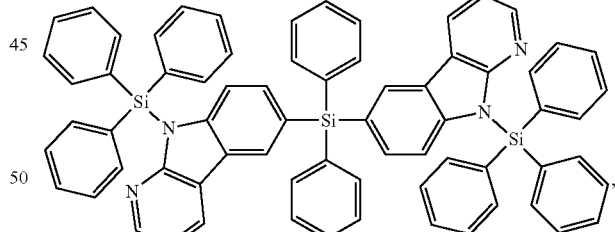

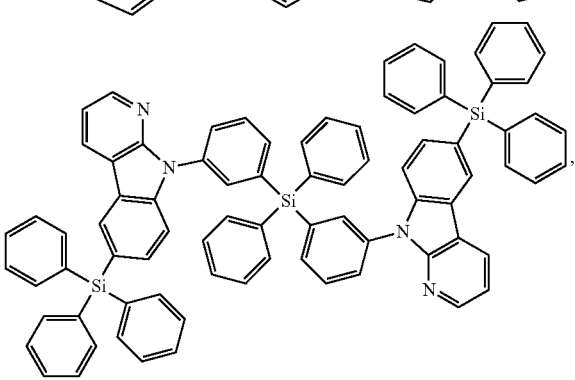

-continued
and
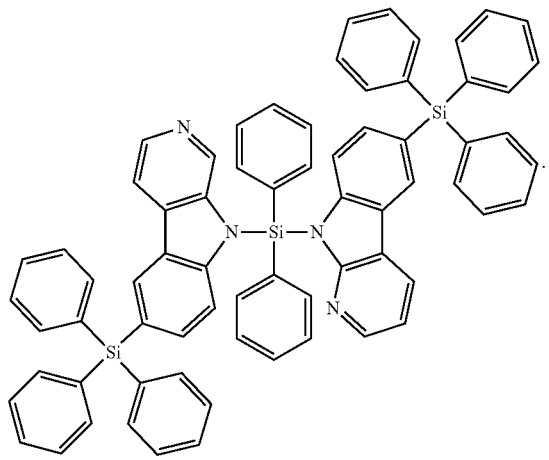
9. The device according to claim 3, wherein the phosphorescent compound is selected from the group consisting of:
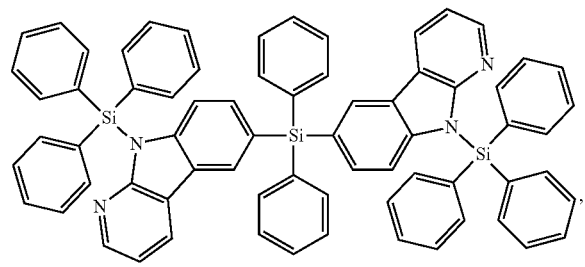
-continued
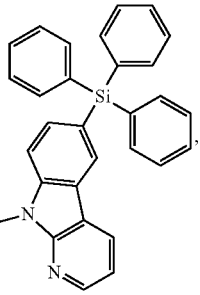
and
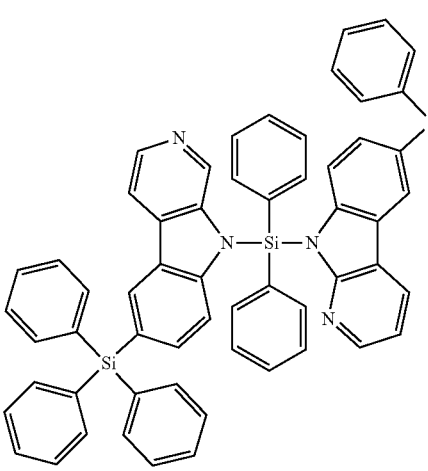
10. The compound according to claim 1, wherein the phosphorescent compound has a triplet energy ($E_T$) above 3.0 eV.
11. The device according to claim 3, wherein the phosphorescent compound has a triplet energy ($E_T$) above 3.0 eV.
* * * * *